United States Patent [19]

Robson et al.

[11] 4,045,416

[45] Aug. 30, 1977

[54] AMINE ACRYLATE ADDITION REACTION PRODUCT COMPOSITIONS

[75] Inventors: John Howard Robson; Erich Marcus, both of Charleston, W. Va.

[73] Assignee: Union Carbide Corporation, New York, N.Y.

[21] Appl. No.: 623,360

[22] Filed: Oct. 17, 1975

Related U.S. Application Data

[60] Division of Ser. No. 499,636, Aug. 22, 1974, Pat. No. 3,963,771, which is a division of Ser. No. 69,136, Sept. 2, 1970, Pat. No. 3,845,056, which is a continuation-in-part of Ser. No. 6,939, Jan. 29, 1970, abandoned.

[30] Foreign Application Priority Data

Jan. 21, 1971  Canada .................................. 103255

[51] Int. Cl.$^2$ ..................... C08F 18/24; C07C 101/20; C07D 51/70

[52] U.S. Cl. ..................... 260/77.5 CR; 204/159.23; 204/159.24; 204/159.22; 106/20; 260/268 PL; 260/268 R; 260/293.63; 260/293.88; 260/335; 260/448.2 B; 260/453 A; 260/453 AR; 260/471 R; 260/471 A; 260/479 R; 260/482 P; 260/486 R

[58] Field of Search ..................... 260/89.5 N, 89.5 R, 260/89.5 A, 77.5 CR; 204/159.22, 159.23; 526/263, 265, 273, 279, 312

[56] References Cited

U.S. PATENT DOCUMENTS

| | | | |
|---|---|---|---|
| 3,845,056 | 10/1974 | Robson et al. | 260/268 R |
| 3,963,771 | 6/1976 | Robson et al. | 260/482 R |

*Primary Examiner*—Richard B. Turer
*Attorney, Agent, or Firm*—Francis M. Fazio

[57] ABSTRACT

Compositions containing an amine acrylate and another radiation curable composition. The amine acrylates are produced by the reaction of a diacrylate ester and an organic amine. The compositions are rapidly cured by electron beam radiation as well as other types of radiation as well as by light curing means; they are useful in the field of protective coatings.

7 Claims, No Drawings

AMINE ACRYLATE ADDITION REACTION PRODUCT COMPOSITIONS

This application is a division of Ser. No. 499,636, filed on Aug. 22, 1974 and issued as U.S. Pat. No. 3,963,771 on June 15, 1974; which was a division of Ser. No. 69,136, filed on Sept. 2, 1970 and issued as U.S. Pat. No. 3,845,056 on Oct. 29, 1974; which was a continuation-in-part of Ser. No. 6,939, filed on Jan. 29, 1970, now abandoned.

Many different coating compositions are known in the art and there is a continuous effort to improve them. In the past many of these coatings contained volatile solvents; however, recently compositions free of such solvents have been in demand to prevent air pollution. Many such improved compositions have found commercial acceptance.

We have now found that certain amine acrylates and compositions thereof are readily cured by ultraviolet radiation, particulate or electron beam radiation or predominantly continuum light radiation. These amine acrylates can be used by themselves to produce protective coatings or they can be mixed with other known coating compositions to enhance the cure rate of these other compositions. It has been found that the amine acrylates of this invention when used in coating compositions cure at extremely rapid rates.

The amine acrylates of this invention are produced by the reaction of a polyacrylate ester, preferably a diacrylate ester with an amine having at least one hydrogen atom attached to the nitrogen atom. Thus, the suitable amines can be the primary amines or the secondary amines; further, they can be monoamines or polyamines. The preferred amine acrylates are the amine diacrylate oligomers. However, polymeric type compositions are also produced and obtained.

In its broader aspects the polyacrylate esters that can be used in the production of the amine polyacrylates are those having the structural formula:

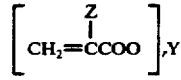

wherein Y is the residue of a polyol (i.e. diol, triol, tetrol) used to produce the polyacrylate ester and $r$ can be an integer having a value of from 2 to 4 depending on whether the polyol was a diol, triol or tetrol. For simplicity, the description will direct itself mainly to those reactions using the diacrylate esters. However, this invention includes the triacrylate esters and the tetraacrylate esters. The amine acrylates produced with these higher functionality esters are generally much more viscous, usually gel-like in nature, and find preferred applications in the production of extruded shaped articles, e.g., tubes, bars, rods, films, etc. In the production of these shaped articles these higher functional amine acrylates are extruded to shape and then cured by exposure to the radiation energy.

The suitable diacrylate esters for producing the amine acrylates have the general structural formula:

wherein Z can be hydrogen or methyl and R is the residue of the diol used to produce the diacrylate ester as hereinafter described.

The production of esters, such as the diacrylate esters, is well known to those of normal skill in the art. It is known that an acid such as acrylic acid or methacrylic acid will react with a dihydroxyl compound or polyhydroxyl compound to produce the diester, or polyacrylate ester. In a simple illustration, acrylic acid reacts with ethylene glycol to produce ethylene glycol diacrylate. The diacrylate esters can also be produced by transesterification reactions. These reactions are known in the art and the conditions under which they are carried out are so well known that they need not be set forth in detail.

The diols that are reacted with acrylic acid or methacrylic acid to produce the diacrylate esters can be any of the compounds containing two hydroxyl groups that will undergo esterification. These are well known and include the aliphatic-type diols having from two to about 20 carbon atoms, such as ethylene glycol, 1,2-propanediol, 1,3-propanediol, 1,2-butanediol, 1,3-butanediol, 1,4-butanediol, 2,3-butanediol, 1,3,3-trimethyl-1,3-propanediol, 2-methyl-2-ethyl-1,3-propanediol, 2-ethyl-1,3-hexanediol, 1,5-pentanediol, 1,10-decanediol, the 5,6-dihydroxyalkylbicyclo[2.2.1]-hept-2-enes having up to about five carbon atoms in the alkyl groups thereof, e.g., 5,6-dihydroxybicyclo[2.2.1]-hept-2-ene, 1-methyl-5,6-dihydroxyethylbicyclo[2.2.1]-hept-2-ene, 5,6-dihydroxymethylbicyclo[2.2.1]hept-2-ene, 5,6-dihydroxyethylbicyclo[2.2.1]hept-2-ene, 5-hydroxy-6-hydroxyethylbicyclo[2.2.1]hept-2-ene, the 5,6-dihydroxypropylbicyclo[2.2.1]hept-2-enes, 5-hydroxymethyl-6-hydroxybutylbicyclo[2.2.1]hept-2-ene, the 5,6-dihydroxypentylbicyclo[2.2.1]hept-2-enes, the 5,6-dihydroxyisopropylbicyclo[2.2.1hept-2-enes, 1,4-cyclohexanedimethanol, p-xylylene glycol, 4-hydroxybenzyl alcohol, 1,4-cyclohexanediol; triols such as trimethylol propane, glycerol, 1,2,6-hexanetriol; tetrols such as pentaerythritrol; and the like; the ether glycols having a molecular weight of from about 106 to about 15,000, including the heteric or block polyoxyalkylene diols, for example, diethylene glycol, triethylene glycol, tetraethylene glycol, dipropylene glycol, tripropylene glycol, dibutylene glycol, the polyethylene glycols and polypropylene glycols having from 2 to about 350 oxyethylene or oxypropylene, respectively, groups in the molecule, the heteric and block poly(ethylene/propylene) glycols having from 2 to about 350 oxyalkylene groups in the molecule, polytetrahydrofurar, and the like; the ester glycols having at least one ester group and two hydroxyl groups in the molecule such as 2,2-dimethyl-3-hydroxypropyl 2,2-dimethyl-3-hydroxypropionate, and the like; the caprolactone polyols disclosed in U.S. Pat. No. 3,169,945 that contain at least two hydroxyl groups and that have a molecular weight of from about 290 to about 20,000, preferably from about 290 to about 2,000. The compounds named and disclosed in U.S. Pat. No. 3,169,945 are incorporated herein by reference. Any dihydroxyl compound can be used that will react with acrylic acid or methacrylic acid to form an ester.

Hence, the residue of the diol used to produce the diacrylate ester, which residue is represented by R, can be a saturated or unsaturated linear or branched polyvalent alkylene wherein the saturated series is represented by the formula —$C_nH_{2n}$— wherein $n$ is an integer having a value of from 2 to about 20 carbon atoms, those skilled in the art know the formulas of unsaturated series, which are preferably non-conjugated; the unsubstituted or substituted divalent bicyclo[2.2.1]hept-5-ene group of the formula:

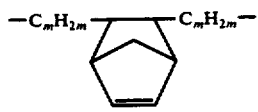

wherein $m$ is an integer having a value of 0 to 5; the unsubstituted or substituted divalent cycloalkylene group of the formula:

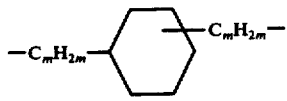

the divalent aralkylene group of the formula:

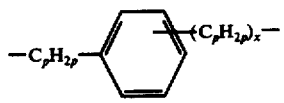

wherein $p$ is from one to about 5 and $x$ is zero or one; the divalent group of the formula:

wherein $y'$ is 1 to about 50; and the divalent group of the formula:

wherein the sum of $z$ plus $z'$ is from 2 to an average total value of about 20 and $R'$ is the residue of the organic functional initiator as said term has been defined and its meaning established in U.S. Pat. No. 3,169,945.

Illustrative of suitable diacrylate esters one can mention those listed in the following tabulation. In said tabulation the group attached to —R— is specifically shown as the acrylyl group. However, it can also be the methacrylyl group; this has not been shown here in order to save space and avoid repetition. The methacrylyl esters are obvious to one skilled in organic chemistry.

TABLE A

Diacrylate Esters of Formula I

1. $CH_2=CHCOO-CH_2CH_2-OOCCH=CH_2$
2. $CH_2=CHCOO-CHCH_2-OOCCH=CH_2$
    $\quad\quad\quad\quad\quad\quad\;\;\;|$
    $\quad\quad\quad\quad\quad\quad\;\;CH_3$
3. $CH_2=CHCOO-CH_2CH_2CH_2CH_2-OOCCH=CH_2$
4. $CH_2=CHCOO-(CH_2)_{10}-OOCCH=CH_2$
5. $CH_2=CHCOO-CHCH_2C-OOCCH=CH_2$ with $CH_3$, $CH_3$ substituents
6. $CH_2=CHCOO-CH_2-C(CH_3)_2-CH_2-OOCCH=CH_2$
7. $CH_2=CHCOO-[bicyclic]-OOCCH=CH_2$
8. $CH_2=CHCOO-CH_2CH_2-[bicyclic]-CH_2CH_2-OOCCH=CH_2$
9. $CH_2=CHCOO-[cyclohexyl]-OOCCH=CH_2$
10. $CH_2=CHCOO-[cyclohexyl, CH_3]-OOCCH=CH_2$
11. $CH_2=CHCOO-CH_2-[cyclohexyl]-CH_2-OOCCH=CH_2$
12. $CH_2=CHCOO-[phenyl]-CH_2=OOCCH=CH_2$
13. $CH_2=CHCOO-CH_2-[phenyl]-CH_2-OOCCH=CH_2$
14. $CH_2=CHCOO-CH_2CH_2OCH_2CH_2-OOCCH=CH_2$
15. $CH_2=CHCOO-CH_2CH_2(OCH_2CH_2)_2-OOCCH=CH_2$
16. $CH_2=CHCOO-CH_2CH_2(OCH_2CH_2)_3-OOCCH=CH_2$
17. $CH_2=CHCOO-CH_2CHOCH_2CH-OOCCH=CH_2$ with $CH_3$, $CH_3$ substituents

TABLE A-continued

Diacrylate Esters of Formula I

18. $CH_2=CHCOO-CH_2CH(OCH_2CH)_{\overline{z}}-OOCCH=CH_2$
    $\quad\quad\quad\quad\quad\quad\quad\quad\;\; |\quad\quad\;\; |$
    $\quad\quad\quad\quad\quad\quad\quad\quad\;\; CH_3\quad CH_3$ 19. $\quad\quad\quad\quad\quad\quad\quad CH_3\quad CH_3$
    $\quad\quad\quad\quad\quad\quad\quad\;\; |\quad\quad\;\; |$
    $CH_2=CHCOO-CH_2CCOOCH_2CCH_2-OOCCH=CH_2$
    $\quad\quad\quad\quad\quad\quad\quad\;\; |\quad\quad\;\; |$
    $\quad\quad\quad\quad\quad\quad\quad\;\; CH_3\quad CH_3$ 20. $CH_2=CHCOO-CH_2CH_2(COOCH_2CH_2)_3-OOCCH=CH_2$
21. $CH_2=CHCOO-(CH_2)_5COOCH_2CH_2OOC(CH_2)_5-OOCCH=CH_2$
22. $CH_2=CHCOO+(CH_2)_5COO]_{\overline{z}}CH_2CH_2OCH_2CH_2+OOC(CH_2)_5]_{\overline{z'}}OOCCH=CH_2$
    $\quad\quad\quad\quad\quad\quad\quad\quad\quad\quad\quad\quad\quad\quad\quad\quad\quad\quad (z + z' = 3.7 \text{ av. sum}).$ 23. $CH_2=CHCOO+(CH_2)_5COO]_{\overline{z}}C_5H_{10}+OOC(CH_2)_5]_{\overline{z'}}OOCCH=CH_2$
    $\quad\quad\quad\quad\quad\quad\quad\quad\quad\quad\quad\quad\quad\quad\quad\quad\quad\quad (z + z' = 4 \text{ av. sum}).$ 24. $CH_2=CHCOO+(CH_2)_5COO]_{\overline{z}}CH_2CH_2(OCH_2CH_2)_4+OOC(CH_2)_5]_{\overline{z'}}OOCCH=CH_2$
    $\quad\quad\quad\quad\quad\quad\quad\quad\quad\quad\quad\quad\quad\quad\quad\quad\quad\quad (z + z' = 4.5 \text{ av. sum}).$ 25. $CH_2=CHCOO+(CH_2)_5COO]_{\overline{z}}CH_2CH+OOC(CH_2)_5]_{\overline{z'}}OOCCH=CH_2$
    $\quad\quad\quad\quad\quad\quad\quad\quad\quad\quad\quad\quad\;\; |$
    $\quad\quad\quad\quad\quad\quad\quad\quad\quad\quad\quad\quad\;\; CH_3$
    $\quad\quad\quad\quad\quad\quad\quad\quad\quad\quad\quad\quad\quad\quad (z + z' = 5 \text{ av.sum}).$ 26. $CH_2=CHCOO+(CH_2)_5COO]_{\overline{z}}CH_2CH(OCH_2CH)_3+OOC(CH_2)_5]_{\overline{z'}}OOCCH=CH_2$
    $\quad\quad\quad\quad\quad\quad\quad\quad\quad\quad\quad\quad\;\; |\quad\quad\quad\quad |$
    $\quad\quad\quad\quad\quad\quad\quad\quad\quad\quad\quad\quad\;\; CH_3\quad\quad\quad CH_3$
    $\quad\quad\quad\quad\quad\quad\quad\quad\quad\quad\quad\quad\quad\quad (z + z' = 3.5 \text{ av. sum}).$ 27. $CH_2=CHCOO+(CH_2)_5COO]\!\!-\!\!\bigcirc\!\!-\!\!+OOC(CH_2)_5]_{\overline{z'}}OOCCH=CH_2$
    $\quad\quad\quad\quad\quad\quad\quad\quad\quad\quad\quad\quad\quad\quad (z + z' = 4.5 \text{ av.sum}).$ 28. $CH_2=CHCOO+(CH_2)_5COO]_{\overline{z}}C_2H_4\!-\!\bigcirc\!\!-\!C_2H_4+OOC(CH_2)_5\, [_{z'} OOCCH=CH_2$
    $\quad\quad\quad\quad\quad\quad\quad\quad\quad\quad\quad\quad\quad\quad (z + z' = 3 \text{ av. sum}).$ 29. $\quad\quad\quad\quad\quad\quad CH_2Br$
    $\quad\quad\quad\quad\quad\quad\;\; |$
    $CH_2=CHCOOCH_2CCH_2OOCCH=CH_2$
    $\quad\quad\quad\quad\quad\quad\;\; |$
    $\quad\quad\quad\quad\quad\quad CH_2Br$ 30. $\quad\quad CH_3\quad\;\; CH_2Br\quad CH_3$
    $\quad\quad\;\; |\quad\quad\quad |\quad\quad\quad |$
    $CH_2=CCOOCH_2CCH_2OOCC=C_2$
    $\quad\quad\quad\quad\quad\quad\;\; |$
    $\quad\quad\quad\quad\quad\quad CH_2Br$ The amines reacted with the diacrylate ester compounds can be any primary or secondary amine, they can be monoamines or polyamines and they can be aliphatic or aromatic, cyclic or acyclic. The suitable amines are those containing at least one reactive hydrogen atom attached to the amine nitrogen atom. Illustrative thereof are the unsubstituted and substituted amines of the following formulas:

$$R''NH_2 \quad\quad\quad\quad II$$

$$\begin{array}{c} R''' \\ | \\ R''NH \end{array} \quad\quad\quad\quad III$$

     IV wherein R" is a linear or branched alkyl having from 1 to about 10 carbon atoms, $(R'''O)_3SiCqH_{2q}$- wherein R''' is alkyl of from 1 to 5 carbon atoms and $q$ is an integer of from 1 to about 5, aryl or aralkyl or alkaryl containing from 6 to about 12 carbon atoms, unsubstituted or substituted cycloalkyl containing from 5 to about 10 carbon atoms; and X is a divalent oxygen atom, a divalent >NH group, a divalent >CR₂"" group wherein R"" can be hydrogen or alkyl of one to five carbon atoms, a divalent >NR''' group, or a divalent

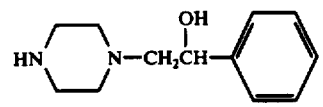

in which $m$ can be zero to 5.

Other suitable amines are the modified piperazine compounds. These include the reaction product of piperazine or alkyl substituted piperazines with mono-epoxides such as epichlorohydrin, styrene oxide, ethylene oxide, propylene oxide, butylene oxide, cyclohexane oxide, and the like, or poly-epoxides such as diglycidyl ether of bisphenol A, 4-vinyl-1-cyclohexene dioxide, and the like; the reaction product of said piperazines with an isocyanate such as phenyl isocyanate, methyl isocyanate, tolylene diisocyanate, bis(2-isocyanatoethyl)bicyclo[2.2.1]-hept-5-ene-2,3-dicarboxylate, bis(2-isocyanatoethyl)4-cyclohexene-1,2-dicarboxylate, and the like. In these instances only one of the >NH groups of the piperazine compound is reacted and there is always an >NH group available from the piperazine molecule. In illustration the product of the reaction of piperazine with styrene oxide yields $$HN\!\!-\!\!\bigcirc\!\!-\!\!N\!-\!CH_2CH\!-\!\bigcirc$$
$$\quad\quad\quad\quad\quad\quad\quad\;\; | $$
$$\quad\quad\quad\quad\quad\quad\quad OH$$

and the product of the reaction with 4-vinyl-1-cyclohexene dioxide yields

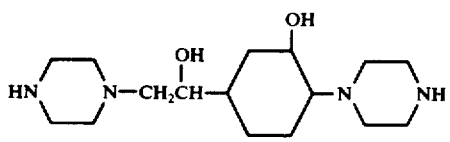

Illustrative of useful amines one can mention methylamine, ethylamine, isopropylamine, n-butylamine, hexylamine, neoheptylamine, 2-ethylhexylamine, decylamine, aminomethyltrimethoxysilane, aminoethyltriethoxysilane, aminoethyltributoxysilane, aminobutyltriethoxysilane, aminopentyltriethoxysilane, aniline, tolylamine, xylylamine, naphthylamine, benzylamine, phenethylamine, cyclopentylamine, methylcyclopentylamine, cyclohexylamine, dimethylcyclohexylamine, dimethylamine, dibutylamine, dioctylamine, N-methylamine, morpholine, piperazine, 2-methylpiperazine, N-methylpiperazine, N-propylpiperazine, piperidine, 2-ethylpiperidine, 4,4'-dipiperidyl, 1,3-di(4-piperidyl)propane, 1,5-di(4-piperidyl)pentane, and the like.

One can also use a polyamine such as ethylenediamine, diethylenetriamine, xylene diamine, hexamethylenetetramine, 1,2-diaminopropane, 1,3-diaminopropane, imino-bis-propylamine, and the like. In such instances one would produce a gel-like amine acrylate compound that can be extruded or molded into a shaped article and then cured by radiation. While amine acrylates produced with polyamines have been made in the past, it has not previously been known or shown that they would rapidly cure to solid, cross-linked materials by the radiation procedures discussed herein.

The amine acrylates are produced by the reaction of a diacrylate ester of formula I with the amine. This reaction is preferably carried out in an inert gas atmosphere, for example, under nitrogen or argon, to prevent or minimize unwanted side reactions. However, this is not necessary for a successful reaction.

The reaction can be carried out at a temperature of from about $-30°$ C. or lower to about 150° C. or higher. The preferred temperature range is from about $-10°$ C. to about 75° C. and the most preferred range is from about 15° C. to about 40° C.

The pressure of the reaction system can be maintained at atmospheric pressure or superatmospheric pressure.

In the reaction, one of the acrylyl groups of the diacrylate ester reacts to displace the amino hydrogen atom while the second acrylyl group of the diacrylate ester is not affected. This reaction can be shown by the following equation:

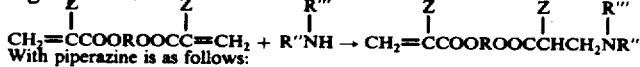
With piperazine is as follows:

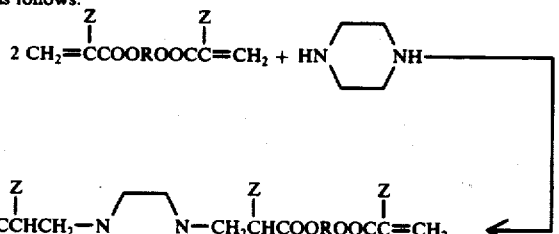

The molar amount of diacrylate ester charged to the reaction system can vary from about 0.9 mole to about 3 moles or more per amino hydrogen atom equivalent in the amino compound to produce the oligomers. The preferred amount of diacrylate ester is at least one mole thereof per amino hydrogen atom equivalent and it is common to use a slight excess of at least about 20 percent. A low molecular weight polymer can be produced by using a lower molar concentration of diacrylate ester; this can be as low as 0.55 mole thereof per amino hydrogen equivalent. This aspect is exemplified in Example 23.

The reaction can be carried out in the absence of a solvent or in the presence of an inert solvent. Among the suitable inert organic solvents that can be used one can mention methanol, ethanol, acetone, benzene, toluene, xylene, hexane, octane, and the like. Any inert solvent can be used that does not interfere with the reaction. In order to minimize side reactions, the reaction is preferably carried out in the absence of light.

In carrying out the reaction the diacrylate ester can be added to the amino compound or the amino compound can be added to the diacrylate ester; the latter procedure is preferred. At the completion of the reaction, the amine acrylates are recovered as residue products; however, in some instances recovery by conventional distillation and fractionation procedures is possible. The amine acrylates can also be prepared by simultaneously spraying separate streams of the amine compound and the diacrylate ester onto a surface or into an enclosed area. In many instances the reaction is rapid and the two components quickly co-react. The means for simultaneously feeding two or more separate streams in the proper ratios are known in the art and such equipment does not constitute a part of this invention.

Among the amine acrylates of this invention are those that can be represented by the general formulas:

 V

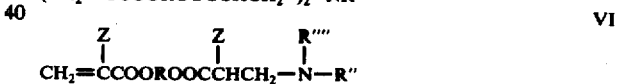 VI

 VII

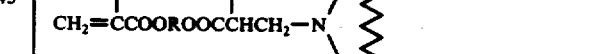 VIII

 IX

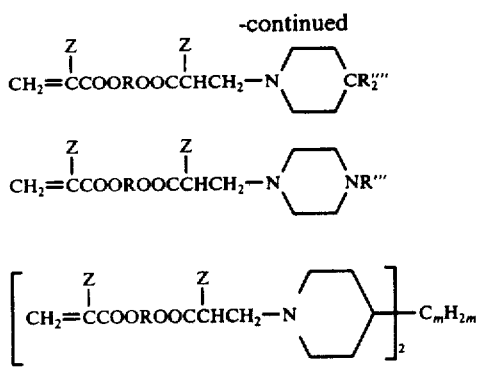

Illustrative of typical amine acrylates produced in this invention one can mention those listed in Table B. In the left hand column of Table B is shown the diacrylate ester from Table A that was used to produce the amine acrylate and in the right hand column there is shown the amine compound that was used to produce the amine acrylate. The amine acrylates produced therefrom correspond to the compounds of Formulas V to XI inclusive as indicated. Thus, when the diacrylate ester used was Compound 1 of Table A and the amine compound was piperazine, the amine acrylate produced was

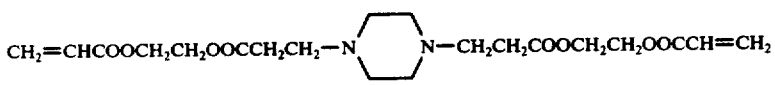

When the dimethacrylate ester of Compound 14 of Table A is reacted with n-hexylamine, the amine acrylate is

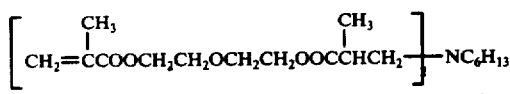

This preceding description will enable any chemist skilled in the art to write out the chemical formula and understand the chemical structures and know the specific amine acrylate compounds set forth in Table B.

TABLE B

| Diacrylate Ester From Table A | Amine Acrylates Amine Compound | Amine Acrylate Formula Type |
|---|---|---|
| Compound 1 | $CH_3NH_2$ | V |
| Compound 8 | $CH_3NH_2$ | V |
| Compound 22 | $CH_3NH_2$ | V |
| Compound 18 | $C_6H_{13}NH_2$ | V |
| Compound 14 | tolylamine | V |
| Compound 19 | Benzylamine | V |
| Compound 21 | cyclohexylamine | V |
| Compound 22 | $(C_2H_5O)_3SiC_3H_6NH_2$ | V |
| Compound 14 | $(C_4H_9O)_3SiC_3H_6NH_2$ | V |
| Compound 6 (1 mole) | $C_6H_{13}NH_2$ | VI |
| Compound 14 | $(CH_3)_2NH$ | VI |
| Compound 17 | $(C_8H_{17})_2NH$ | VI |
| Compound 14 | N-methylpiperazine | VI |
| Compound 3 | piperazine | VII |
| Compound 8 | piperazine | VII |
| Compound 11 | piperazine | VII |
| Compound 22 | piperazine | VII |
| Compound 26 | piperazine | VII |
| Compound 14 | 2-methylpiperazine | VII |
| Compound 2 | morpholine | VIII |
| Compound 7 | morpholine | VIII |
| Compound 10 | morpholine | VIII |
| Compound 21 | morpholine | VIII |
| Compound 6 | piperazine | IX |
| Compound 14 | piperazine | IX |
| Compound 19 | piperazine | IX |
| Compound 23 | 2-ethylpiperidine | IX |
| Compound 15 | piperidine | IX |

TABLE B-continued

| Diacrylate Ester From Table A | Amine Acrylates Amine Compound | Amine Acrylate Formula Type |
|---|---|---|
| Compound 1 | N-methylpiperazine | X |
| Compound 4 | N-methylpiperazine | X |
| Compound 9 | N-pentylpiperazine | X |
| Compound 14 | N-isopropylpiperazine | X |
| Compound 18 | N-ethylpiperazine | X |
| Compound 25 | N-ethylpiperazine | X |
| Compound 6 | 4,4'-dipiperidyl | XI |
| Compound 11 | 4,4'-dipiperidyl | XI |
| Compound 24 | 4,4'-dipiperidyl | XI |
| Compound 6 | 1,3-di(4-piperidyl)propane | XI |
| Compound 8 | 1,3-di(4-piperidyl)propane | XI |
| Compound 19 | 1,5-di(4-piperidyl)pentane | XI |

As previously indicated the amine acrylates are readily cured by ultraviolet light radiation or electron beam radiation or high intensity predominantly continuum light radiation. The curing is very rapid and a durable protective film is formed. One can also cure the compositions in a molded or extruded form to produce intricately shaped articles such as rods, tubes, films and the like.

The coating compositions can be applied to a surface by any of the known conventional means, including the spray, curtain, dip, pad and roll-coating techniques. The substrate to be coated can be any composition; for example, wood, metal, paper, plastic, fabric, fiber, ceramic, concrete, plaster, glass, etc.

The amine acrylate-containing compositions can be cured by ionizing radiation, either particulate or non-particulate, or non-ionizing radiation. As a suitable source of particulate radiation, one can use any source which emits electrons or charged nuclei. Particle radiation can be generated from electron accelerators such as the Van de Graaff, resonance transformers, linear accelerators, insulating core transformers, radioactive elements such as cobalt-60, strontium-90, etc. As a suitable source of non-particulate ionizing radiation, one can use any source which emits radiation in the range of from about $10^{-3}$ Angstroms, to about 2000 Angstroms, preferably from about $5 \times 10^{-3}$ Angstroms to about 1 Angstrom. Suitable sources are vacuum ultraviolet lamps, such as xenon or krypton arcs, mercury lamps, and radioactive elements such as cesium-137, strontium-90 and cobalt-60. The nuclear reactors are also known to be a useful source of radiation. As a suitable source of non-ionizing radiation, one can use any source which emits radiation of from about 2000 Angstroms to about 4500 Angstroms. Suitable sources are mercury arcs, carbon arcs, tungsten filament lamps, xenon arcs, krypton arcs, sunlamps, lasers, and the like. All of these devices and sources are well known in the art and those familiar with the technology are fully aware of the manner in which the radiation is generated and the precautions to be exercised in its use.

The ionizing radiation dosage necessary to effect cross-linking will vary depending upon the particular polymer that is undergoing radiation, the extent of crosslinking desired, the number of crosslinkable sites available and the molecular weight of the starting polymer. The total dosage will be from about $10^{-3}$ rads to $10^{-8}$ rads, preferably from $5 \times 10^{-3}$ rads to $10^{-7}$ rads. A rad is 100 ergs of ionizing energy absorbed per gram of material being irradiated.

The radiation is carried out at a temperature below the decomposition temperature of the resin undergoing treatment, generally it is preferably from about −80 to about 125° C.

The use of low to high pressure mercury lamps to generate ultraviolet light is known. The largest such mercury lamp of commercial utility is generally about 5 feet long having a diameter of about one to two inches with an electrical input of about 20 kilowatts generating a typical low intensity ultraviolet light line structure (source intensity is generally no greater than about 20 kilowatts per square foot of source projected area). An appreciable period of time is generally needed for completion of a reaction when a material is exposed to the low intensity ultraviolet radiation generated from a mercury lamp.

It has been indicated that high intensity predominantly continuum light radiation can also be used to cure or crosslink the amine acrylates or compositions containing the amine acrylates.

Recently a source of light radiation emitting high intensity predominantly continuum light radiation containing ultraviolet, visible and infrared radiation that can be used to polymerize monomers and to crosslink polymer compositions was discovered, namely the swirl-flow plasma arc radiation source. By means of proper light filters one can selectively screen out a portion of the light radiation emitted permitting only that wavelength portion desired to reach the material being treated.

The term "high intensity predominantly continuum light radiation" means continuum radiation with a source intensity of at least 350 watts per square centimeter steradian (about 1000 kilowatts per square foot) having only a minor part of the energy in peaks of bandwidths less than 100 Angstrom units, with less than about 30 percent of the light radiated having wavelengths shorter than 4,000 Angstrom units and at least about 70 per cent of the light energy radiated having wavelengths longer than 4,000 Angstrom units.

This light radiation is derived from an artificial source that generates high intensity predominantly continuum light radiation with a source intensity of at least about 350 watts per square centimeter steradian, as abreviated by the term: watts $cm^{-2}sr^{-1}$; said high intensity predominantly continuum artificial light radiation has about 7 per cent of the light radiated at a wavelength longer than 4,000 Angstroms and less than about 30 per cent of the light radiated having a wavelength shorter than 4,000 Angstroms, generally about 80 per cent of the light radiated has a wavelength longer than 4,000 Angstroms and less than about 20 per cent of the light radiated has a wavelength shorter than 4,000 Angstroms, and a source intensity that can vary from about 350 watts (about 1,000 kilowatts per square foot of source projected area) to about 5,000 watts (about 15,000 kilowatts per square foot of source projected area) or more per square centimeter steradian. A convenient source of high intensity predominantly continuum light radiation is a swirl-flow plasma arc light radiation apparatus. The equipment for generating high intensity predominantly continuum light radiation by this means is known and available; many different forms thereof are described in the literature. A highly efficient apparatus for obtaining high intensity predominantly continuum light radiation is the swirl-flow plasma arc radiation source described in U.S. Pat. No. 3,364,387. The apparatus or equipment necessary for generating the light radiation is not the subject of this invention and any source or apparatus capable of generating high intensity predominantly continuum light radiation can be used.

While any artificial source of generating high intensity predominantly continuum light radiation can be used, as previously indicated the swirl-flow plasma arc radiation apparatus is most convenient. Hence, this source will be used in this application as illustrative of a means for obtaining the high intensity continuum light radiation. Any apparatus that operates according to the known principles of the swirl-flow plasma arc radiation source can be used to produce the high intensity predominantly continuum light radiation useful in the processes of this invention. These apparatuses are often known by other terms by those skilled in this art recognize that they emit high intensity predominantly continuum light radiation. The source of radiation in a 50 kilowatt swirl-flow plasma arc radiation source is an arc only about four inches long enclosed in a quartz envelope about 1.5 inches in diameter. This lamp can be readily removed and refurbished and has an acceptable long lifetime. Further, a swirl-flow plasma arc radiation apparatus having a 250-kilowatt rating would be only about two or three times as large as a 50-kilowatt source. Another advantage is the absence of a need for expensive radiation shielding. Precautions required for the artificial light sources include those needed to protect one's eyes from the intense visible light and from the ultraviolet light present to prevent inadvertent sunburn effect on the body.

It is to be noted that in the spectra of high intensity predominantly continuum light radiation there is a continuum of radiation throughout the entire spectral range. This type of continuum radiation in the ultraviolet range has not heretofore been obtainable from the conventional commercial mercury arcs or lamps generally available for generating ultraviolet light. The previously known means for generating ultraviolet light produced light that shows a line or peak spectrum in the ultraviolet range, it is not a continuum spectrum in the ultraviolet range. In a line spectrum the major portion of useable ultraviolet light is that portion at which the line or band in the spectrum forms a peak; in order for such energy to be useful the material or composition that is to be treated with ultraviolet radiation must be capable of absorbing at that particular wavelength range at which the peak appears. In the event the material or composition does not have the ability to absorb at that particular wavelength range there is little or no absorption or reaction. Thus, in the event the material or composition to be treated absorbs at a particular wavelength range in one of the valleys of the spectral curve there will be little or no reaction since there is little or no ultraviolet energy to adequately excite the system. With a high intensity predominantly continuum radiation, there is a high intensity continuum radiation of ultraviolet energy across the entire ultraviolet wavelength range of the spectrum and there is generally sufficient ultraviolet energy generated at all useful ultraviolet wavelengths to enable one to carry out reactions responsive to ultraviolet radiation without the problem of selecting compounds that will absorb at the peak wavelength bands only. With the high intensity continuum radiation now discovered one does not have the problem of being unable to react materials or compositions that absorb in the valley areas only since for all intents and purposes such valleys do not exist in high intensity continuum radiation, the high intensity radiated light energy is essentially a continuum, it is not in peak bands.

High intensity predominantly continuum light radiation is to be distinguished from low intensity ultraviolet radiation generated by commercially available low, medium and high pressure mercury are ultraviolet lamps. These mercury arc lamps produce light emission which is primarily line or peak rather than continuum light, wherein a major part of the light appears in bands narrower than 100 Angstrom units, and much less than 70 per cent is above 4,000 Angstrom units.

As is known, high intensity predominantly continuum light radiation from a swirl-flow plasma arc radiation source is emitted from an arc generated between a pair of electrodes that are lined up axially and encased in a quartz cylinder. In an embodiment a pair of concentric quartz cylinders between which cooling water or gas flows is used. A rare gas, such as argon, krypton, neon or xenon, introduced into the inner cylinder tangentially through inlets located at one end of the inner cylinder, creates a swirling flow or vortex which restricts the arc to a small diameter. An electrical potential applied across the electrodes cause a high density current to flow through the gas to generate a plasma composed of electrons, positively charged ions and neutral atoms. A plasma generated in the above gases produces high intensity predominantly continuum light radiation with diffuse maxima in the region of from about 3,500 to about 6,000 Angstroms. The radiation source can also be used with reflectors or refractive optical systems to direct the high intensity predominantly continuum light radiation emanating from the arc to a particular point or direction or geometrical area.

Crosslinking with the predominantly continuum light radiation from a swirl-flow plasma arc radiation source is usually carried out at ambient temperature. The time necessary for curing the amine acrylate-containing compositions will vary from a fraction of a second to 30 seconds or more. In some instances as much as several minutes may be required if a thick, pigmented layer is being cured. The necessary time for completion of curing is dependent upon the particular amine acrylate used as well as any other component that may be present in the coating composition.

The rate of curing can be enhanced by the addition of suitable photosensitizers. Illustrative of suitable photosensitizer compounds one can mention acetophenone, propiophenone, benzophenone, xanthone, fluorenone, benzaldehyde, fluorene, anthraquinone, triphenylamine, carbazole, 3- or 4-methylacetophenone, 3- or 4-pentylacetophenone, 3- or 4-methylbenzophenone, 3- or 4-chlorobenzophenone, 4,4'-bis(dimethylamino)benzophenone, 4,4'-dimethoxybenzophenone, 4-chloro-4'-benzylbenzophenone, 3-chloroxanthone, 3,9-dichloroxanthone, 3-chloro-8-nonylxanthone, 3-methoxyxanthone, 3-iodo-7-methoxyxanthone, and the like. As is obvious one can use a mixture of photosensitizers. The amount of photosensitizer used can vary from about 0.01 to about 20 weight per cent of the coating solution. A preferred amount is from about 0.1 to about 5 weight per cent, and most preferred is a concentration of from about 0.5 to about 3 weight per cent.

As previously indicated the amine acrylates, singly or in mixtures, can be blended with from 1 to about 50 weight per cent or more of other coating compositions that are known to cure on exposure to radiation. The concentration of amine acrylates blended in such compositions can vary from about 1 to 99.9 weight per cent of the coating composition, preferably from about 10 to about 75 weight per cent. These coating compositions can also contain from about 5 to about 50 weight per cent of a polymerizable solvent such as styrene or a high boiling acrylyl ester.

The high boiling acrylyl esters that are useful in this invention can contain more than one acrylyl group in the molecule; they are well known in the art and can be represented by the general formula:

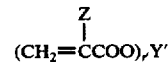

wherein Z can be hydrogen or methyl; $r'$ is an integer having a value of from 1 to about 4; and Y' can be Y or it can be a monovalent group such as hydrogen; alkyl of from 1 to about 18 carbon atoms (e.g. methyl, ethyl, propyl, isopropyl, butyl, isobutyl, t-butyl, pentyl, hexyl, 2-methylhexyl, 2,3-dimethylbutyl, neopentyl, heptyl, neohexyl, 3,3-dimethylpentyl, octyl, 2-ethylhexyl, nonyl, decyl, etc.); alkoxyalkyl having up to about 15 carbon atoms (e.g. methoxymethyl, methoxybutyl, methoxydecyl, ethoxyethyl, ethoxyoctyl, butoxyethyl, butoxypropyl, hexoxyethyl, decoxyethyl, decoxypentyl, etc.); haloalkyl, wherein the alkyl group has up to about 15 carbon atoms as defined above and the halogen can be fluorine, chlorine, bromine or iodine (e.g. chloromethyl, chlorodecyl, fluoroethyl, bromoethyl, iodomethyl, dichloroethyl, perfluoroisopropyl, trichlorobutyl, etc.); cyano; cyanoalkyl wherein the alkyl group has up to about 15 carbon atoms as defined above (e.g. cyanomethyl, cyanoethyl, cyanobutyl, cyanodecyl, etc.); epoxyalkyl wherein the alkyl group has up to about 15 carbon atoms as defined above (e.g. glycidyl, 4,5epoxypentyl, 2,3-epoxycyclohexyl, etc.); aryl (e.g. phenyl, xylyl, tolyl, naphthyl, naphthal, benzyl, etc.); aryloxyalkyl wherein the alkyl group has up to about 15 carbon atoms as defined above (e.g. 2-phenoxyethyl, 10-phenoxydecyl, 2-tolyloxyethyl, 2-naphthyloxyethyl, etc.); trialkoxysilyloxyalkyl wherein the alkoxy group has from 1 to about 5 carbon atoms and the alkyl group has up to about 15 carbon atoms as defined above (e.g. trimethoxysilyloxymethyl, trimethoxysilyloxypropyl, trimethoxysilyloxydecyl, triethoxysilyloxyethyl, triethoxysilyloxybutyl, tripropoxysilyloxyethyl, tributoxysilyloxyethyl, etc.); —CONG$_2$, wherein G can be hydrogen or hydrocarbyl having up to about 15 carbon atoms (e.g. N-methyl, N-ethyl, N-propyl, N-butyl, N-decyl, N,N-dimethyl, N,N-diethyl, N,N-diisobutyl, N-cyclohexyl, N,N-dicyclohexyl, N-phenyl, N-naphthyl, N-methyl-N-phenyl, N,N-diphenyl, N-benzyl, N,N-dibenzyl, N-tolyl, etc.); dicyclopentenyl; bicyclo[2.2.1]-hept-2-en-5-yl; bicyclo[2.2.1]hept-2-en-5-yl; bicyclo[2.2.1]hept-2-en-5-yl-alkyl, wherein the alkyl group has from 1 to about 4 carbon atoms (e.g. bicyclo[2.2.1]-hept-2-en-5-ylmethyl, bicyclo[2.2.1]hept-2-en-5-ylpropyl, etc.). As indicated Y' can also be Y; in such instances it is a polyvalent group such as divalent —C$_p$H$_{2p}$-group wherein p has a value of from 1 to about 10 (e.g. methylene, ethylene, propylene, isopropylene, butylene, hexylene, 2,2-dimethylbutylene, 2-ethylhexylene, decylene, etc.); —C$_r$H$_{2r}$(OC$_r$H$_{2r}$)$_v$— wherein r has a value of from 2 to about 4 and v has a value of from 1 to about 5000 and the oxyalkylene portion thereof can be oxyethylene, oxypropylene, 2-oxypropylene, oxybutylene, or mixed oxyalkylene groups in the same molecule, etc.;

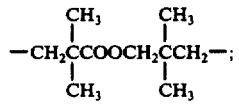

formula-$C_tH_{2t-1}$-wherein $t$ has a value of from 3 to about 10 (e.g.

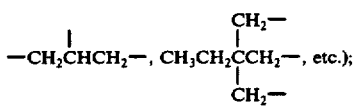

aliphatic hydrocarbon of the formula-$C_sH_{2s-2}$-wherein $s$ has a value of from 4 to about 10 (e.g.

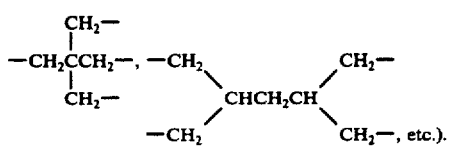

These high boiling acrylyl compounds are well known in the art and many of them are described in "Vinyl and Related Polymer" by C. E. Schildknecht, published in 1952 by John Wiley and Sons. The common knowledge of these compounds makes the specific naming thereof in this application unnecessary in view of the extensive description set forth above.

The coating compositions are produced by mixing the selected components thereof by conventional known methods. The blend can be heated, if desired, to facilitate mixing.

Coating compositions having the amine acrylate compound present, alone or in admixture, can contain fillers, pigments and other additives conventionally present in coating compositions. These additives are so well known to those skilled in the art that they need no specific mention; nor is it necessary for an understanding of this invention to recite concentrations thereof. The same can be said of the known radiation curable coating compositions that can be admixed with the amine acrylates to improve the curing and crosslinking properties.

The following examples serve to further describe this invention. The structures were confirmed by nuclear magnetic resonance spectrum analysis.

EXAMPLE 1

There was charged to a reaction flask 53.5 grams of diethylene glycol diacrylate and, while stirring, there was added in a dropwise manner at 20° C. a solution of 8.6 grams of piperazine in 22 ml. of anhydrous methanol. The reaction mixture was stirred for an additional hour at 20° C. and the methanol was stripped off. There was recovered 60 grams of a residue, which was a colorless liquid containing the amine acrylate having the following formula, as confirmed by nuclear magnetic resonance spectrum analysis.

The amine acrylate was used to coat metal panels, and the coated panels were exposed to different types of radiation. When exposed to beta radiation from a 300-kilovolt electron beam accelerator under a nitrogen atmosphere, the coating was cured to a smooth surface with a 0.5-megarad dose.

A mixture of this amine acrylate with 3 weight per cent of benzophenone cured in 3 seconds under a 550-watt medium-pressure mercury arc. This same mixture was completely cured in 0.5 second when exposed to the predominantly continuum light radiation from a 50-kilowatt argon swirl-flow plasma arc radiation source.

EXAMPLE 2

In a manner similar to that described in Example 1, 32.2 grams of diethylene glycol diacrylate was reacted with 8.6 grams of piperazine in 22 ml. of anhydrous methanol. There was recovered 42.4 grams of the liquid, colorless amine acrylate as a residue product after removal of methanol at reduced pressure.

The amine acrylate was blended with 3 weight per cent of benzophenone and it was used to coat a steel panel. This coating cured in 0.2 seconds to a dry tack-free film when exposed to the predominantly continuum light radiation from a 50-kilowatt argon swirl-flow plasma arc radiation source. The coating was smooth and had good impact resistance.

EXAMPLE 3

In a manner similar to that described in Example 1, 212 grams of neopentyl glycol diacrylate was reacted with 34.4 grams of piperazine in 88 ml. of anhydrous methanol. After removing methanol under vacuum, there was recovered 244.1 grams of the liquid, colorless amine acrylate having the following structural formula:

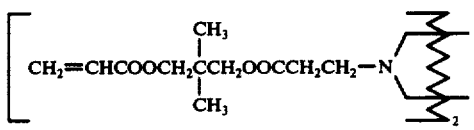

This amine acrylate was blended with 3 weight per cent of benzophenone, and the blend was applied as a coating to a steel panel. The coating cured in 1.3 seconds on exposure to the predominantly continuum light radiation from a 50-kilowatt argon swirl-flow plasma arc radiation source. The coating was smooth and had good impact resistance.

EXAMPLE 4

In a manner similar to that described in Example 1, 21.2 grams of neopentyl glycol diacrylate was reacted with a solution of 10.5 grams of 1,3-di(4-piperidyl)propane in 25 ml. of anhydrous methanol. After removal of methanol under vacuum, there was recovered 32.8 grams of the liquid, colorless amine acrylate of the following structural formula:

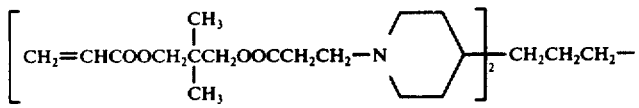

A portion of this amine acrylate was blended with 3 weight per cent of benzophenone and coated on a steel panel as a film. This coating cured in 0.8 seconds on exposure to the predominantly continuum light radiation from 50-kilowatt argon swirl-flow plasma arc radiation source. The coating was smooth and had good impact properties.

EXAMPLE 5

To 42.4 grams of neopentyl glycol diacrylate there was added at 20° C., in a dropwise manner, 10.1 grams of n-hexylamine. After the addition was completed, the mixture was stirred at 20° C. for 15 minutes, then heated to 40° C. and stirred for an additional 2 hours. The amine acrylate solution was a colorless mixture of the two products shown in the following formulas: the individual components were present in a ratio of 3 parts of A to 2 parts of B.

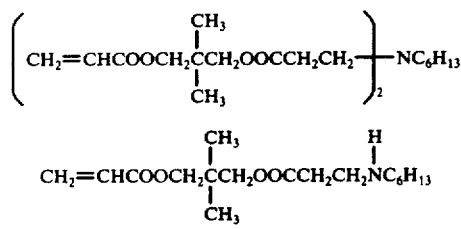

A portion of this amine acrylates mixture was blended with 3 weight per cent of benzophenone and coated on a steel panel. The coating cured in 2.4 seconds on exposure to the predominantly continuum light radiation from a 50-kilowatt argon swirl-flow plasma arc radiation source. The coating had good impact properties.

When the neopentyl glycol diacrylate was replaced with ethylene glycol diacrylate and the reaction carried out under the same conditions, there was obtained a colorless liquid solution that was a mixture of the amine acrylates having the following structural formulas:

$(CH_2=CHCOOCH_2CH_2OCH_2CH_2OOCCH_2CH_2)_2NC_6H_{13}$

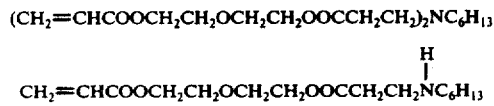

This solution cured to a tack-free film when treated in the same manner as the immediately preceding amine acrylates mixture.

EXAMPLE 6

In a manner similar to that described in Example 1, 25.44 grams of neopentyl glycol diacrylate was reacted with 10 grams of N-methylpiperazine. There was obtained a colorless solution of amine acrylate having the following structural formula:

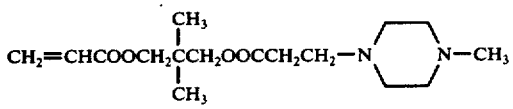

A portion of this amine acrylate was blended with 3 weight per cent of benzophenone and coated on steel panels. The coatings cured to tack-free films in 10 seconds on exposure to the predominantly continuum light radiation from a 50-kilowatt argon swirl-flow plasma arc radiation source.

A series of experiments was carried out to produce different amine acrylates. The procedure followed was similar to that described in Example 1. When the amine compound was a solid it was initially dissolved in anhydrous methanol and slowly added to the stirred diacrylate. When the amine was a liquid it was added in a dropwise manner to the diacrylate. Methylamine was added as a 40 per cent aqueous solution, and the water was subsequently removed by azeotropic distillation with benzene. In all instances the reaction was carried out under a nitrogen atmosphere and in an amber glass reactor or a reactor wrapped in aluminum foil for the exclusion of light. The concentrations of the reactants and the amine acrylates produced are shown in the following table. Also shown in this table are the properties of coating on steel panels. These coatings were obtained by blending the amine acrylate with 3 weight per cent of benzophenone and coating a steel panel. The coatings were cured by exposure to the predominantly continuum light radiation from a 50-kilowatt argon swirl-flow plasma arc radiation source.

| | Reactants | | | Cure Time | Impact In-lb | | Sward Hardness | Coating Properties | | | | |
| | Diacrylate | | Amine | | | | | Adhesion | | | | |
| Ex | Name | Moles | Name | Moles | Seconds | Reverse | Front | | % | $H_2O$ | EtOH | $NaOH^a$ | $H_2SO_4^b$ |
|---|---|---|---|---|---|---|---|---|---|---|---|---|---|
| 7 | NPGDA | 1.5 | Piperazine | 1.0 | 1.3 | 165 | 165 | 4 | 100 | 10 | 10 | 0 | 0 |
| 8 | NPGDA | 2.0 | Methylamine | 1.0 | 1.3 | 165 | 165 | 12 | 0 | 10 | 10 | 0 | 2 |
| 9 | NPGDA | 1.5 | Methylamine | 1.0 | 0.6 | 165 | 165 | 4 | 0 | 10 | 10 | 0 | 2 |
| 10 | NPGDA | 1.25 | Methylamine | 1.0 | 0.5 | 165 | 165 | 6 | 100 | 10 | 10 | 0 | 2 |
| 11 | NPGDA | 2.0 | APTS | 1.0 | 2.1 | 165 | 165 | 6 | 100 | 10 | 10 | 0 | 1 |
| 12 | NPGDA | 1.5 | APTS | 1.0 | 1.3 | 165 | 165 | 8 | 100 | 10 | 10 | 0 | 2 |
| 13 | NPGDA | 1.25 | APTS | 1.0 | 1.2 | 165 | 165 | 6 | 100 | 10 | 10 | 0 | 2 |
| 14 | DEGDA | 2.0 | Methylamine | 1.0 | 1.2 | 100 | 165 | 6 | 0 | 3 | 10 | 0 | 1 |
| 15 | DEGDA | 1.5 | Methylamine | 1.0 | 0.6 | 165 | 165 | 6 | 100 | | | | |
| 16 | DMHP | 2.0 | Piperazine | 1.0 | 2.0 | 165 | 165 | 0 | 100 | 7 | 0 | 0 | 1 |

| | Reactants | | | | Cure Time Seconds | Coating Properties | | | | | | | |
|---|---|---|---|---|---|---|---|---|---|---|---|---|---|
| | Diacrylate | | Amine | | | Impact In-lb | | Sward Hardness | Adhesion % | $H_2O$ | EtOH | NaOH[a] | $H_2SO_4$[b] |
| Ex | Name | Moles | Name | Moles | | Reverse | Front | | | | | | |
| 17 | DEGCDA | 2.0 | Methylamine | 1.0 | 2.3 | 165 | 165 | 10 | 100 | 3 | 10 | 0 | 1 |

[a]Twenty per cent solution at 25° C. for 24 hours.
[b]Three per cent solution at 25° C. for 24 hours.
NPGDA - Neopentyl glycol diacrylate
DEGDA - Diethylene glycol diacrylate
APTS - gamme-Aminopropyltriethoxysilane
DMHP - 2,2-Dimethyl-3-hydroxypropyl 2,2-dimethyl-3-hydroxy-propionate
DEGCDA - Compound 22, Table A Sward Hardness was determined using the procedure set forth on page 138 of the Paint Testing Manual published by Gardner Laboratory, Inc., P. O. Box 5728, Bethesda, Md. The impact test procedure is described on page 146 of the same manual. Adhesion was determined by scribing the film with a sharp knife into ten one-eighth inch squares, pressing scotch tape firmly against the test surface at a 45° angle to the square and pulling the tape away with one quick motion. The percent adhesion is then determined visually.

The amine acrylate produced in Example 7 has the structure shown in Example 3. The amine acrylate of Examples 8 to 10 has the structure:

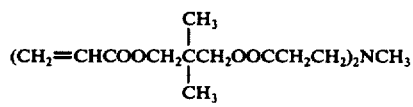

The amine acrylate of Examples 11 to 13 has the structure:

$(CH_2=CHCOOCH_2\overset{CH_3}{\underset{CH_3}{C}}CH_2OOCCH_2CH_2)_2NC_3H_6Si(OC_2H_5)_3$ The amine acrylate of Examples 14 and 15 has the structure:

$(CH_2=CHCOOCH_2CH_2OCH_2CH_2OOCCH_2CH_2)_2NCH_3$

The amine acrylate of Example 16 has the structure:

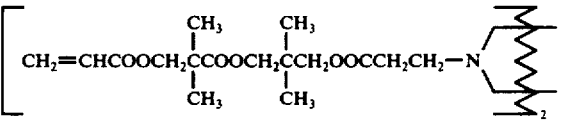

The amine acrylate of Example 17 has the structure:

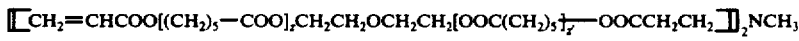

wherein the sum of $z$ plus $z'$ is an average total value of 3.7.

EXAMPLE 18

A reactor was charged with 3180 grams of neopentyl glycol diacrylate and there was bubbled into the stirred diacrylate 310 grams of methylamine at a temperature of 20° C. The amine acrylate produced was a colorless liquid having a Brookfield viscosity of 1175 cps. at 25° C. This amine acrylate is a mixture of compounds having the structural formula:

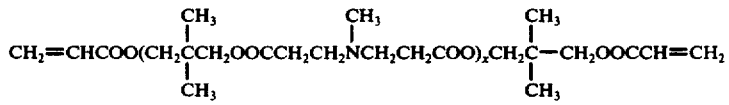

wherein $x$ has a value of from 1 to 4. Coatings on steel panels with 3 weight per benzophenone and without benzophenone cured to dry films on exposure to the predominantly continuum light radiation from a 50-kilowatt argon swirl-flow plasma arc light radiation source.

EXAMPLE 19

A. A resin was prepared by reacting 21.4 grams of a caprolactone polyol, which was the reaction product of one mole of trimethylolpropane with caprolactone to an average molecular weight of about 535, with 15.5 grams of 80/20 mixture of 2,4- and 2,6-tolylene diisocyanate and 13.9 grams of 2-hydroxyethyl acrylate. The resin has the basic structural formula:

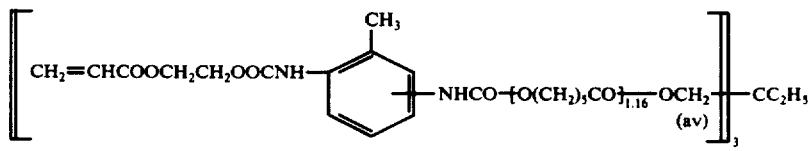

B. An amine acrylate was prepared in a manner similar to that described in Example 1 by slowly adding 25 parts by weight of morpholine to 75 parts by weight of neopentyl glycol diacrylate contained in an amber reactor in an inert atmosphere. The amine acrylate has the structure:

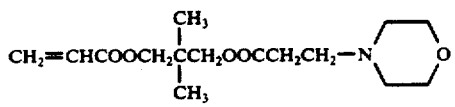

C. A solvent solution was prepared containing equal part of 2-ethylhexyl acrylate and 2-butoxyethyl acrylate.

A series of coating composition was prepared containing different amounts of the resin (A), solvent solution (C) and amine acrylate (B). These coating compositions were blended with 3 weight percent benzophenone and the coatings were applied to steel panels. The coatings were cured by exposure to the predominantly continuum light radiation from a 50-kilowatt argon swirl-flow plasma arc radiation source to produce dry films. The compositions of the coatings and the exposure times are tabulated below:

| Coating | A Resin (Parts) | C Solvent Parts | B Amine Acrylate (Parts) | Exposure to Cure (sec) | Sward Hardness (Glass = 100) |
|---|---|---|---|---|---|
| (1) | 50 | 45 | 5 | 10 | 6 |
| (2) | 50 | 40 | 10 | 8 | 4 |
| (3) | 50 | 35 | 15 | 5 | 4 |
| (4) | 50 | 30 | 20 | 4 | 4 |
| (5) | 50 | 25 | 25 | 3 | 2 |

EXAMPLE 20

A. A resin was prepared as described in Section (A) of Example 19. This resin had the same basic structure as set forth therein.

B. An amine acrylate was prepared as described in Section (B) of Example 19, having the same basic structure as set forth therein.

A series of coating compositions was prepared, each containing 50 parts of Resin (A). Compositions (1) to (7) contained 10 parts of Amine Acrylate (B). Each composition contained 3 parts of benzophenone. In addition, each composition contained polymerizable acrylate monomers as indicated in the table. The coating compositions were applied as 0.5 to 0.7 mil wet films on steel panels and cured by radiation at a distance of 3.5 inches with electrons from a 300-kilovolt electron beam; they were also cured by exposure to the predominantly continuum light radiation from a 50-kilowatt argon swirl-flow plasma arc radiation source at a distance of two feet from the arc and at a distance of four feet from an 80-kilowatt argon swirl-flow plasma arc radiation source.

| No. | Coating Compositions — Parts of Polymerizable Acrylates |
|---|---|
| (1) | 17 parts 2-butoxyethyl acrylate |
|  | 10 parts 2-ethoxyethyl acrylate |
|  | 10 parts diethylene glycol diacrylate |
| (2) | 10 parts 2-ethoxyethyl acrylate |
|  | 10 parts diethylene glycol diacrylate |
|  | 17 parts 2-hydroxyethyl acrylate |
| (3) | 17 parts 2-ethylhexyl acrylate |
|  | 10 parts 2-ethoxyethyl acrylate |
|  | 10 parts diethylene glycol diacrylate |
| (4) | 27 parts 2-ethoxyethyl acrylate |
| (5) | 10 parts diethylene glycol diacrylate |
|  | 27 parts 2-ethoxyethyl acrylate |
|  | 10 parts neopentyl glycol diacrylate |
| (6) | 32 parts 2-ethoxyethyl acrylate |
|  | 5 parts diethylene glycol diacrylate |
| (7) | 32 parts 2-ethoxyethyl acrylate |
|  | 5 parts neopentyl glycol diacrylate |

The coatings cured under the electron beam had the following properties; all were given an eight magarad dose.

| Coating Comp. | Extractables** mg./sp. in. | Sward Hardness | Reverse Impact in.-lb. | Chemical Resistance** 1% $H_2SO_4$ | 50% $C_2H_5OH$ |
|---|---|---|---|---|---|
| (1) | 0.47 | 30 | >165 | 9 | 8 |
| (2) | 0.48 | 34 | 50 | 10 | 8 |
| (3) | 0.55 | 30 | >165 | 9 | 8 |
| (4) | 0.45 | 32 | 50 | 9 | 8 |
| (5) | 0.59 | 38 | 50 | 9 | 8 |
| (6) | 0.71 | 32 | >165 | 9 | 8 |
| (7) | 0.47 | 34 | >165 | 9 | 8 |

*Reflux extraction with 10 per cent ethanol for 24 hours
**Scale of 10 used in all tables The coatings cured by exposure to the light radiation from the 50-kilowatt argon swirl-flow plasma arc radiation source had the following properties: All of the coatings showed a reverse impact value greater than 165 in.-lb.

| Coating Comp. | Exposure Sec. | Extractables mg./sq. in. | Sward Hardness | Chemical Resistance 1% $H_2SO_4$ | 50% $C_2H_5OH$ |
|---|---|---|---|---|---|
| (1) | 5 | 0.52 | 26 | 10 | 9 |
| (2) | 5 | 0.23 | 34 | 4 | 7 |
| (3) | 5 | 0.42 | 28 | 10 | 9 |
| (4) | 4 | 0.41 | 28 | 10 | 10 |
| (5) | 4 | 0.42 | 28 | 10 | 10 |
| (6) | 3 | 0.36 | 22 | 10 | 10 |
| (7) | 3 | 0.45 | 22 | 10 | 9 |

The coatings cured by exposure to the light radiation from the 80-kilowatt argon swirl-flow plasma arc radiation source had the following properties. All of the coatings were exposed for 2.7 seconds and all showed a reverse impact value greater than 165 in.-lb.

| Coating Comp. | Sward Hardness | Chemical Resistance 1% $H_2SO_4$ | 50% $C_2H_5OH$ |
|---|---|---|---|
| (1) | 28 | 9 | 7 |
| (2) | 32 | 9 | 9 |
| (3) | 34 | 8 | 9 |
| (4) | 44 | 10 | 9 |
| (5) | 44 | 8 | 10 |
| (6) | 30 | 10 | 10 |
| (7) | 26 | 10 | 9 |

EXAMPLE 21

A series of ink formulations was prepared by blending different colors of conventional ink pigments with an amine acrylate prepared as described in Example 3. In these ink formulations 85 grams of the amine acrylate, 15 grams of ink pigment and 3 grams of benzophenone were blended together in a pebble mill. The inks were applied to steel panels and then cured by exposure to the predominantly continuum light radiation from a 50-kilowatt argon swirl-flow plasma arc radiation source. In all cases the printing inks had good impact properties and adhesion; they were hard and glossy and they did not smear. The results are tabulated below:

| Pigment Name | Wt. % | Cure Time Seconds | Impact[a] Reverse | Front | Sward[b] Hardness | Adhesion[c] | $H_2O$ | EtOH | NaOH[d] | $H_2SO_4$[e] |
|---|---|---|---|---|---|---|---|---|---|---|
| Black | 15 | 3.2 | 165 | 165 | 16 | 100 | 9 | 9 | 0 | 2 |
| Chrome Yellow | 15 | 1.1 | 165 | 165 | 2 | 100 | 10 | 9 | 0 | 0 |
| Blue | 15 | 1.3 | 165 | 165 | 6 | 100 | 5 | 2 | 0 | 0 |
| $TiO_2$ | 15 | 5.5 | 165 | 165 | 2 | 90 | 10 | 6 | 0 | 0 |
| Red | 15 | 3.6 | 165 | 165 | 12 | 100 | 10 | 9 | 0 | 3 |

[a]Gardner Impact Test.
[b]Glass equals 100.
[c]Scotch tape cross-hatch test.
[d]Twenty per cent solution at 25° C. for 24 hours.
[e]Three per cent solution at 25° C. for 24 hours.

What is claimed is:

1. A pigmented or unpigmented composition comprising from 1 to 99.9 weight percent of at least one amine acrylate, said amine acrylate being the addition reaction product of a primary or secondary organic amine and a polyacrylate, said reaction product being selected from the group of:

  or

wherein
Z is hydrogen or methyl
R" is alkyl of from 1 to 5 carbon atoms, cycloalkyl of from 5 to 10 carbon atoms, or aryl or aralkyl or alkaryl of from 6 to 12 carbon atoms;
R"" is hydrogen or alkyl of from 1 to 5 carbon atoms; and
R is the residue of a diol of the group of saturated aliphatic diols having from 2 to 20 carbon atoms, bicyclo[2.2.1]hept-2-ene diols, cyclohexyl diols, phenyl and mono-and di- lower alkyl phenyl diols, polyalkylene ether diols having from 2 to 4 carbon atoms in the alkylene group and ester glycols having from 1 to an average of 17.5 ester groups; and
x has a value of from 1 to 4; in admixture with at least one other radiation curable composition.

2. A composition as claimed in claim 1 wherein the amine acrylate has the formula:

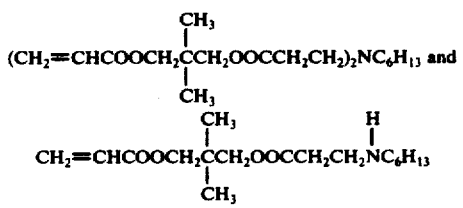

3. A composition as claimed in claim 1 wherein the amine acrylate has the formula:

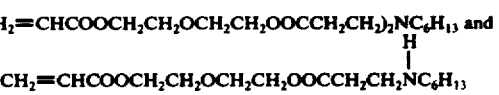

4. A composition as claimed in claim 1 wherein the amine acrylate has the formula:

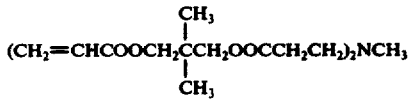

5. A composition as claimed in claim 1 wherein the amine acrylate has the formula:
$(CH_2=CHCOOCH_2CH_2OCH_2CH_2OOCCH_2CH_2)_2NCH_3$ 6. A composition as claimed in claim 1 wherein the amine acrylate has the formula:

wherein the sum of z plus z' is an average total value of 3.7.

7. A composition as claimed in claim 1 wherein the amine acrylate has the formula:

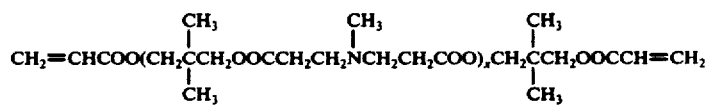

wherein x has a value of from 1 to 4.

* * * * *